United States Patent [19]

Mittleman et al.

[11] Patent Number: 4,534,764
[45] Date of Patent: Aug. 13, 1985

[54] SEQUENTIAL MEDICATION DELIVERY DEVICE

[75] Inventors: Herbert Mittleman, Deerfield; Stanislaw Sulek, Chicago, both of Ill.

[73] Assignee: Trimedyne, Inc., Santa Ana, Calif.

[21] Appl. No.: 517,224

[22] Filed: Jul. 25, 1983

[51] Int. Cl.³ .............................................. A61M 5/00
[52] U.S. Cl. .................................... 604/81; 604/150; 604/90
[58] Field of Search .................... 604/81, 80, 90, 150; 137/109, 113; 222/145

[56] References Cited

U.S. PATENT DOCUMENTS

| | | | |
|---|---|---|---|
| 3,199,511 | 8/1965 | Kulick | 604/150 |
| 4,141,379 | 2/1979 | Manske | 604/81 X |
| 4,324,238 | 4/1982 | Genese et al. | 604/81 |

Primary Examiner—Stephen C. Pellegrino

[57] ABSTRACT

A sequential medication delivery device for intravenous administration of plural medications is disclosed. A secondary medication can be administered to a patient followed by an automatic resumption of the delivery of the primary medication at a predetermined flow rate. The disclosed medication delivery device includes an internal valving system and an associated medication chamber that contains the secondary medication to be delivered. While the medication chamber contains such secondary medication, the flow of primary medication to the patient is interrupted. However, once the medication chamber has been substantially emptied the flow of primary medication to the patient is resumed automatically.

22 Claims, 4 Drawing Figures

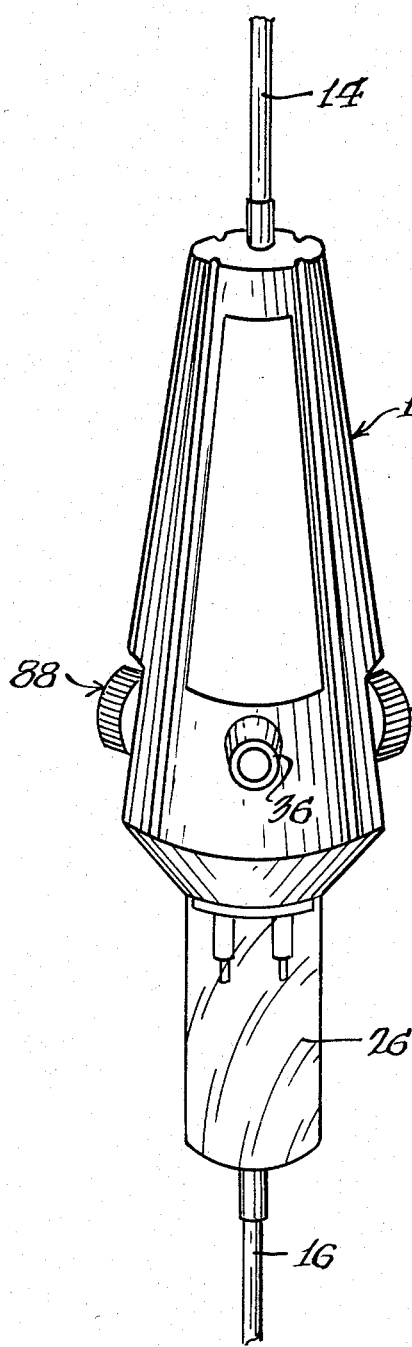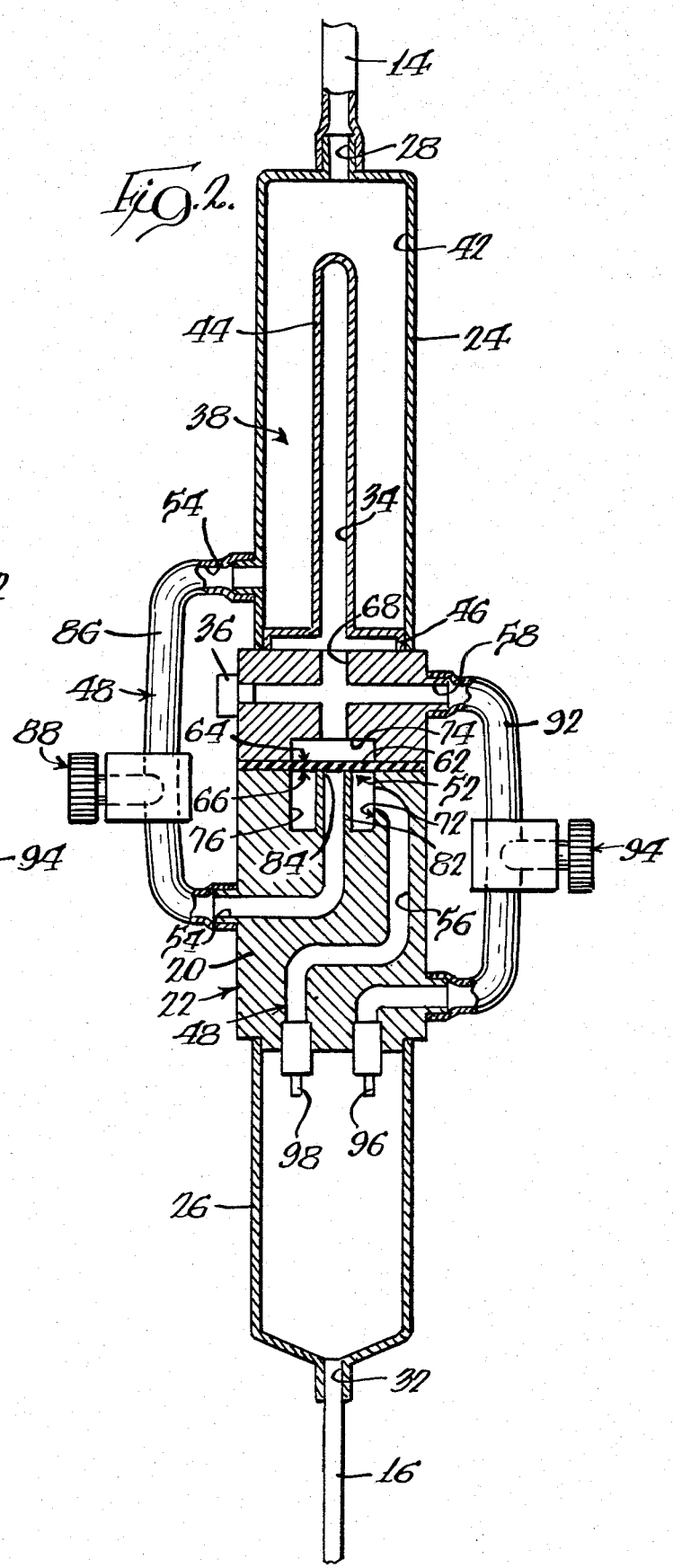

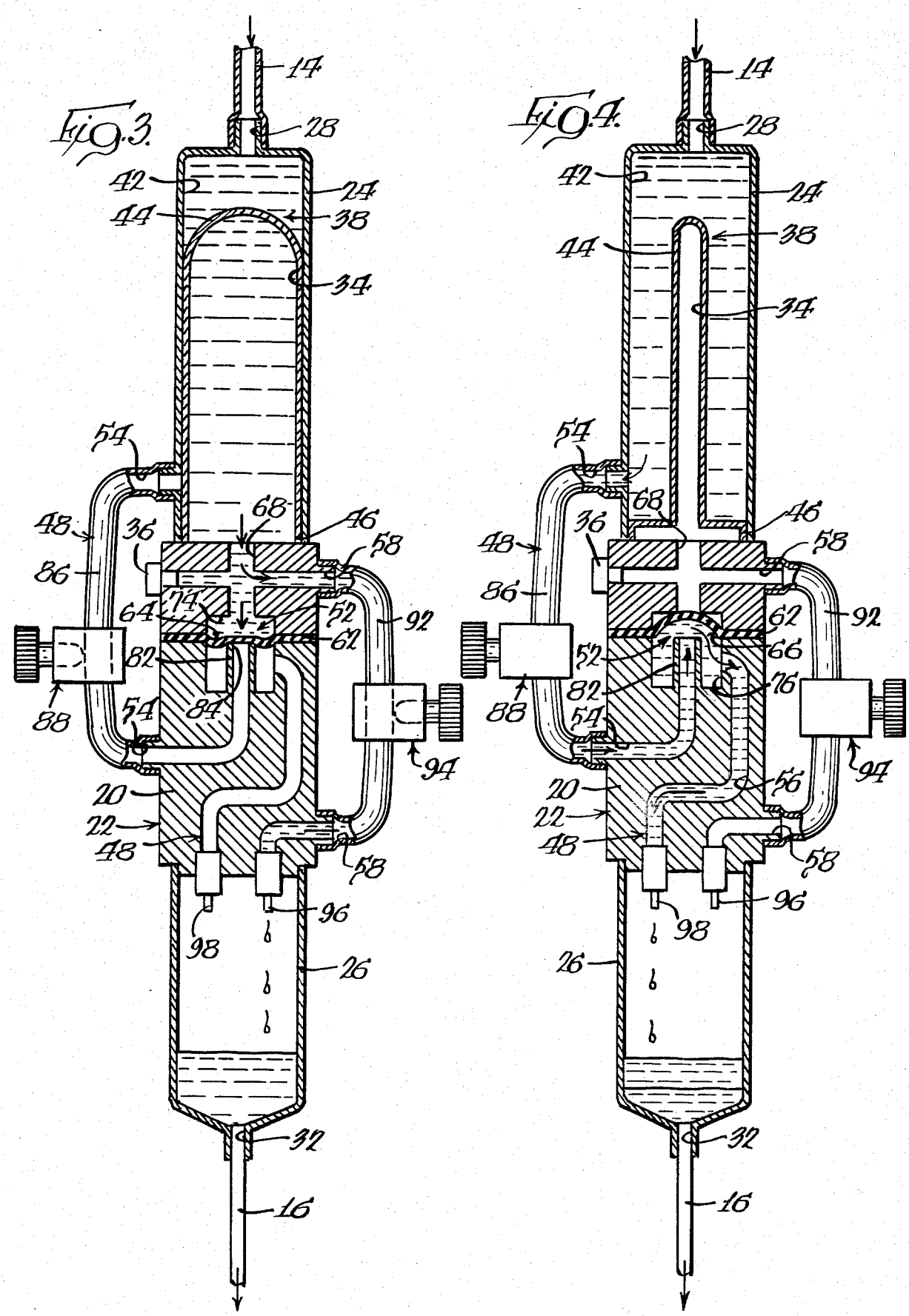

SEQUENTIAL MEDICATION DELIVERY DEVICE

TECHNICAL FIELD OF THE INVENTION

The present invention relates to medical devices which administer medications to a patient sequentially.

BACKGROUND OF THE INVENTION

Medications are often administered to a patient intravenously by what is known as a piggy-back set-up. Generally, in such a system a catheter is located in a patient's vein and connected by a delivery tube to a "Y" connector. One branch of the connector is coupled through a one-way valve to a primary reservoir which contains a primary medication that is to be administered for a prolonged time period, e.g., saline, dextrose, or the like liquids. The other branch of the connector is coupled to a secondary reservoir into which a secondary medication has been placed with or without dilution.

For proper system valve operation, the secondary reservoir must be hung higher than the primary reservoir. This generates a greater head of pressure from the secondary reservoir to maintain the valve in a closed position, preventing the flow of primary medication. When the secondary reservoir is exhausted, its head of pressure drops and the valve opens, allowing the flow of primary medication to the patient. See for example U.S. Pat. Nos. 4,237,880 to Genese 4,256,103 to Mylrea and 4,258,712 to Harms et al.

Piggy-back systems unfortunately require two reservoirs, one for the primary medication and one for the secondary medication. Such systems also require two separate sets of tubing, a connector, a valve device, and related flow control apparatus. Such an extensive amount of equipment not only complicates the use of the system, but also greatly adds to its cost. Additional tubes are necessary where it is desired to provide different administration rates for the primary and secondary medications. Control of administration can also be complicated by the varying relative heads of pressure in the two reservoirs and the need to properly locate the reservoirs with respect to each other. Other devices require that air be admitted to displace medication, thus creating the risk of contamination.

Accordingly, it is desirable to provide a medical device which avoids the shortcomings of prior systems and automatically sequentially administers plural medications to a patient. The device of the present invention meets these desires and avoids the necessity of two reservoirs that must be positioned at certain respective elevations. The present device also has a relatively uncomplicated structure and is relatively easy to use.

SUMMARY OF THE INVENTION

The present invention is a sequential medication delivery device which can automatically administer an additive or secondary medication to a patient followed by a resumption of primary medication delivery. Medications to be administered can be of any type suitable for liquid delivery.

The medication delivery device generally includes an internal valving system and an associated medication chamber which is adapted to receive the secondary medication and is in fluid communication with an outlet. An inlet adapted to be placed in fluid communication with a source of primary medication is also provided as part of the device. The inlet is in fluid communication with a volume reducing means for reducing the volume of the medication chamber so as to deliver medication from that chamber to the outlet.

The medication delivery device also includes a liquid passageway for the flow of liquid between the inlet and outlet and hence from the primary medication source to the patient. Valve means are provided for occluding the liquid passageway to interrupt the flow of primary medication from the inlet to the outlet until substantially all of the medication as been delivered from the chamber. Thereafter, the primary medication is free to flow to the patient.

The volume reducing means preferably includes a flexible partition separating an enclosure from the medication chamber. The enclosure is in fluid communication with the inlet such that the fluid pressure at the inlet pressurizes the medication chamber across the partition to provide substantially equal driving pressure for both medications. This avoids the necessity of having medication reservoirs at a specific elevation relative to one another as is common in the prior art. There also is no need for a separate reservoir for the additive or secondary medication beyond that provided within the medical device of the present invention.

The valve means preferably is a gating member such as a flexible diaphragm having one side associated with the secondary medication chamber and the other side associated with the liquid passageways delivering the primary medication. The side associated with the liquid passageway preferably has a smaller relative surface area than the side associated with the medication chamber. The total force on the secondary medication side is then greater than on the primary medication side until substantially all of the secondary medication has been delivered from the chamber.

For ease of construction, the inlet, outlet, enclosure, medication chamber, and valve means can be in a single housing. Only two tubes need extend from the medical device, one to the primary medication source and one to the patient. This not only greatly simplifies the use of the device, but also reduces its cost. Flow regulating means can also be provided to independently regulate the flow of the medications.

Numerous other advantages and features of the present invention will become readily apparent from the following detailed description of the invention, the drawings, and the appended claims.

BRIEF DESCRIPTION OF THE DRAWINGS

FIG. 1 is an external elevational view of medical device embodying the present invention;

FIG. 2 is the enlarged schematic representation of the internal structure of the medical device of FIG. 1;

FIG. 3 shows the medical device administering medication from a medication chamber forming part of the device; and FIG. 4 shows the medication device administering a primary medication from a conventional source (not shown) in communication with the inlet forming part of a device.

DETAILED DESCRIPTION OF THE PREFERRED EMBODIMENT

While the present invention can be embodied in many different forms, there is shown in the drawings, and will be described in detail, a preferred embodiment of the invention. The present disclosure is a exemplification of the principles of the present invention and is not intended to limit the invention to the embodiment illustrated.

The exterior structure of a medical device emboding the present invention can best be seen in FIG. 1. The exterior structure includes a case 12 which protects the internal components, an inlet tube 14, which is placed in fluid communication with a primary medication source (not shown), and an outlet tube 16 which is placed in fluid communication with the patient (not shown). Further details of the device are described below.

Referring also to FIG. 2, the medical device generally includes a housing 22 having a main body portion 20, a container 24 and a drip chamber such as an optically transparent cell 26. The inlet tube 14 and outlet tube 16 are respectively associated with the medical device through an inlet 28 and an outlet 32 both of which are preferably part of the housing 22.

The medical device also includes a medication chamber 34 adapted to receive and hold the additive or secondary medication. This medication can be introduced into the medication chamber 34 through an injection port 36 with a hypodermic syringe or similar device. The injection port 36 includes a septum of a resealing material such as silicone rubber. Volume reducing means 38 is placed in fluid communication with the inlet 28 for reducing the volume of the medication chamber 34 to deliver the secondary medication from the chamber to the outlet 32. The volume reducing means preferably includes an enclosure 42 separated from the medication chamber by a partition 44. As shown, the enclosure 42 is defined in part by the housing container 24.

The partition 44 is preferably of a flexible and liquid impermeable material such as natural or silicone rubber, or a thermoplastic material such as polyethelyene. As shown, the partition 44 can have a generally bag or balloon-like configuration with a closed end extending into the container 24, and an open end 46 mounted on the main body portion 20 of the housing 22. For ease of construction and operation, the partition and hence the medication chamber 34 and enclosure 42 are located within the container 24.

The total volume defined by the container 24 remains constant while the relative volumes of the chamber 34 and enclosure 44 change as the secondary medication is delivered. As the primary medication enters through the inlet 28, it generates a pressure within the enclosure 42 which is transmitted through the flexible partition 44 into the medication chamber 34. This equalizes the pressure between the medications and thus avoids the necessity of specific relative location of the reservoirs containing the respective medications. Since the volume of the medication chamber is reduced, no air need be admitted to dispense the secondary medication. This, of course, greatly reduces the risk of contamination.

Primary medication flows from the inlet 28 to the outlet 32 through a liquid passageway 48 which is defined in part by the enclosure 42. Valve means 52 occludes the liquid passageway 48 to interrupt the flow of primary medication to the outlet 32 until substantially all of the secondary medication has been delivered from the chamber 34. The liquid passageway 48 includes a first fluid passageway 54 in fluid communication between the inlet 28 and the valve means 52, and a second fluid passageway 56 in fluid communication between the valve means and the outlet 32. The second fluid passageway 56 as shown is defined by the housing main body portion 20 and the drip chamber or cell 26. The chamber 34 communicates with the outlet 32 through a secondary medication passageway 58 also defined in part by the housing 22.

The valve means 52 preferably includes a gating member 62 having a first side 64 associated with the chamber 32 and a second side 66 associating with the liquid passageway 48. Until substantially all of the secondary medication has been delivered from the chamber, the total force on the first side 64 is greater than the total force on the second side 66. The first side 64 is in fluid communication with the medication chamber 34 via an opening 68 over a first surface area. The second side 66 of the member 62 is in fluid communication with the liquid passageway over a second surface area. The second surface area is less than the first surface area. Since the pressures per unit area on both sides of the member 62 are relatively the same when there is medication in the chamber 34, the force on the first side 64 is therefore greater than that on the second side 62. This keeps the valve means 52 closed until substantially all of the secondary medication has been delivered.

The gating member 62 is preferably a diaphragm which divides a cavity 72 defined by the housing 22 into a secondary medication compartment 74 and a primary medication compartment 76. The diaphragm gating member 62 is preferably of an elastomeric material such as a natural or silicone rubber, but can also be made to be a thermoplastic material such as polypropylene, polyethylene, or the like. The gating member 62 can be captured between two halves of the main body portion 20 of the housing 22 as shown in FIGS. 2-4.

The first fluid passageway 54 preferably communicates with the liquid compartment 76 by a hollow stem 82 which extends into the liquid compartment. The surface area of the member 62 defined by the cross-sectional area of the passageway of the hollow stem 82 is the second surface area of the member described above.

As can be seen in FIGS. 2-4, this second surface area is substantially smaller than the first surface area defined by the medication compartment 74 adjacent the gating member 62. The projecting end 84 of the stem 82 also occupies a portion of the diaphragm surface 66, thus further reducing the surface which can be subjected to liquid pressure.

The end 84 of the stem 82 engages and seals with gating member 62 until substantially all of the secondary medication has been administered to the patient. End 84 of the stem 82 can be provided with a series of concentric ridges that further enhance sealing with the member 62. At rest position, the gating member 62 is in contact with the stem end 84 and with no tension against the stem end.

The first fluid passageway 54 preferably is defined in part by a primary medication hose 86 which can be adjustably occluded by primary medication flow regulating means 88. The first fluid passageway 54 can also be defined in part by the enclosure 42 between the hose 86 and the inlet 28 with the remainder of the first fluid passageway defined by the main body portion 20 and the stem 82. The secondary medication passageway is preferably defined in part by a secondary medication hose 92 which can be adjustably constricted by secondary medication flow regulating means 94. The hoses 86, 92 are preferably of a flexible material such as Silastic, a trademark of Dow Corning Corp. of Midland, Mich.

The flow regulating means 88 and 94 operate independently, and preferably have a generally screw-type construction allowing a wide variety of settings. This makes it relatively easy to independently set the administration rates of the medication in a compact medical device. The medications drip into the top portion of the cell 26 through cannulas 96 and 98 producing drops having predetermined volume. This allows for easy adjustment of the flow rate by simply counting the number of drops per unit time.

In use, the medical device is connected to a primary medication reservoir through the inlet tube 14 and to the patient through the outlet tube 16 after any air in the device or outlet tube 16 has been purged. The administration rate for the primary medication is then set with the flow regulating means 88. The secondary medication is then injected through the injection port 36 into the medication chamber 34. The medical device then assumes the configuration generally shown in FIG. 3. The desired administration rate for the secondary medication is then set by flow regulating means 94.

The pressure is substantially the same in the medication chamber 34 as in the enclosure 42 and the liquid in the stem 82. The greater surface area of the gating member 62 on the medication chamber side as compared to the surface area defined by the stem 82 keeps the gating member 62 sealingly engaged with the stem end 84. This prevents the flow of primary medication through the liquid passageway 48 while secondary medication is contained in chamber 34.

After substantially all of the medication has been delivered from the chamber 34 as shown in FIG. 4, the pressure in the medication chamber and hence the medication compartment 74 is reduced. The total force on the second side 66 of the member 62 then exceeds the total force on the first side 64 causing the member to be moved away from the stem end 84. As a result, primary medication will then flow from the stem 82 through the compartment 76 and out through the second fluid passageway 56 as shown in FIG. 4. The opening 68 between the medication chamber 34 and the medication compartment 74 is sufficiently small to prevent the flexible partition 44 from being forced through that opening and coming into direct contact with the diaphragm 68 so as to avoid interference with the operation of the valve means 52.

If desired, an additional bolus of secondary medication can be injected into the chamber 34. This will automatically reset the valve means 52 to seal the liquid passage 48 until the injected bolus of secondary medication has been administered.

What is claimed is:

1. A sequential medication delivery device for administering plural medications to a patient, the device comprising:
   (a) an inlet means for receiving a primary medication from a primary medication source;
   (b) an outlet means for placement in fluid communication with the patient;
   (c) a liquid passageway means in fluid communication between the inlet means and the outlet means;
   (d) a housing defining a chamber adapted to receive a secondary medication and in fluid communication with the outlet means; the housing also including a volume reducing means in fluid communication with the inlet means for reducing the volume of the chamber to deliver secondary medication from the chamber to the outlet means; and
   (e) valve means for occluding the liquid passageway means until substantially all of the secondary medication has been delivered from the chamber.

2. The medication delivery device of claim 1 wherein the volume reducing means includes a partition defining a portion of the chamber and an enclosure in fluid communication with the inlet means, the partition separating the enclosure from the chamber.

3. The medication delivery device of claim 2 wherein the partition is made of flexible material.

4. The medication delivery device of claim 1 wherein the valve means includes a gating member having a first side in fluid communication with the chamber and a second side in fluid communication with the liquid passageway means such that until substantially all of the secondary medication has been delivered, the force on the first side is greater than the force on the second side.

5. The medication delivery device of claim 4 wherein the gating nember is a flexible diaphragm.

6. The medication delivery device of claim 4 where in the first side of the gating member is in fluid communication with the chamber over a first surface area and the second side is in fluid communication with the liquid passageway means over a second surface area, the first surface area being larger than the second surface area.

7. The medication delivery device of claim 1 wherein the valve means includes a cavity defined by a housing and divided by a diaphragm into a medication compartment in fluid communication with the chamber, and a liquid compartment in fluid communication with the liquid passageway means by a hollow stem extending into the liquid compartment with the diaphragm sealingly engaging the end of the stem to prevent the flow of primary medication through the stem until substantially all of the secondary medication has been delivered.

8. The medication delivery device of claim 1 further including primary medication flow regulating means associated with the liquid passageway means for regulating the flow of primary medication through the liquid passageway means.

9. The medication delivery device of claim 1 further including secondary medication flow regulating means for regulating the flow of secondary medication from the chamber to the outlet means.

10. The medication delivery device of claim 1 further including an optically clear cell defining the outlet means and receiving the medications prior to delivery to the patient.

11. The medication delivery device of claim 1 wherein the secondary medication chamber communicates with the outlet means through a flexible hose.

12. The medication delivery device of claim 1 wherein at least a portion of the liquid passageway means is defined by a flexible hose.

13. The medication delivery device of claim 1 including an injection port associated with the chamber for introducing secondary medication into the chamber.

14. A sequential medication delivery device for administering a primary and secondary medication to a patient, the device comprising:
   (a) a housing defining an enclosure and a medication chamber separated by a flexible partition;
   (b) an inlet means on the housing in fluid communication with the enclosure and adapted to be placed in fluid communication with a primary medication source;
   (c) an outlet means adapted to be placed in fluid communication with the patient;
   (d) valve means carried by the housing;

(e) a first fluid passageway means in fluid communication with the inlet means and the valve means;

(f) a second fluid passageway means in fluid communication with the valve means and the outlet means;

(g) a secondary medication passageway means in fluid communication with the chamber, the valve means and the outlet means such that a positive pressure at the inlet means generates a positive fluid pressure in the enclosure to drive the partition to displace secondary medication in the chamber; the valve means interrupting the flow of primary medication from the first fluid passageway means to the second fluid passageway means until substantially all the secondary medication has been displaced from the chamber.

15. The medication delivery device of claim 14 wherein the valve means includes a gating member having a first side in fluid communication with the chamber and a second side in fluid communication with the first passageway means such that until substantially all of the secondary medication has been delivered to the patient, the force on the first side is greater than the force on the second side.

16. The medication delivery device of claim 15 wherein the gating member is a flexible diaphragm.

17. The medication delivery device of claim 15 wherein the first side of the gating member is in fluid communication with the medication passageway means over a first surface area and the second side is in fluid communication with the first passageway means over a second surface area, the first surface area being larger than the second.

18. The medication delivery device of claim 14 wherein the valve means includes a secondary medication compartment defined by the housing in fluid communication with the medication passageway means, a primary medication compartment in fluid communication with the second passageway means, and a hollow stem in fluid communication with the first passageway means and extending into liquid compartment such that the diaphragm sealingly engages with the end of the stem to prevent the flow of primary medication through the stem into the primary medication compartment until substantially all of the secondary medication has been delivered.

19. The medication delivery device of claim 14 wherein the housing includes an optically clear cell carrying the outlet means.

20. The medication delivery device of claim 14 wherein the first fluid passageway means is defined in part by the enclosure.

21. The medication delivery device of claim 14 further including secondary medication flow regulating means associated with the secondary medication passageway and primary medication flow regulating means associated with the first fluid passageway for independently regulating the flow of primary and secondary medications to the patient.

22. A sequential medication delivery device for administering medications to a patient, the device comprising:

(a) a housing defining an enclosure and a chamber separated by a flexible partition;

(b) an inlet means;

(c) an outlet means in fluid communication with the chamber;

(d) a primary medication compartment in fluid communication with the outlet means;

(e) a secondary medication compartment in fluid communication with the chamber;

(f) a diaphragm separating the medication compartments; and (g) a hollow stem in fluid communication with the inlet means and extending into the primary medication compartment such that the diaphragm engages and seals with the stem until substantially all of the liquid contents has been delivered from the chamber.

* * * * *